US008758625B2

(12) United States Patent
Kato et al.

(10) Patent No.: US 8,758,625 B2
(45) Date of Patent: Jun. 24, 2014

(54) USE OF POROUS HOLLOW-FIBER MEMBRANE FOR PRODUCING CLARIFIED BIOMEDICAL CULTURE MEDIUM

(75) Inventors: Chihiro Kato, Tokyo (JP); Yuukou Seki, Tokyo (JP); Satoshi Shiki, Tokyo (JP)

(73) Assignees: Asahi Kasei Chemicals Corporation, Tokyo (JP); Asahi Kasei Medical Co., Ltd., Tokyo (JP)

( * ) Notice: Subject to any disclaimer, the term of this patent is extended or adjusted under 35 U.S.C. 154(b) by 313 days.

(21) Appl. No.: 13/120,753

(22) PCT Filed: Sep. 25, 2009

(86) PCT No.: PCT/JP2009/066670
§ 371 (c)(1),
(2), (4) Date: May 9, 2011

(87) PCT Pub. No.: WO2010/035793
PCT Pub. Date: Apr. 1, 2010

(65) Prior Publication Data
US 2011/0210067 A1  Sep. 1, 2011

(30) Foreign Application Priority Data

Sep. 26, 2008 (JP) ................ P2008-248766
Sep. 26, 2008 (JP) ................ P2008-248804

(51) Int. Cl.
*B01D 61/00* (2006.01)
*B01D 69/08* (2006.01)
*B01D 71/68* (2006.01)
*B01D 71/26* (2006.01)
*B01D 39/00* (2006.01)

(52) U.S. Cl.
CPC ..................................... *B01D 61/00* (2013.01)
USPC . 210/650; 210/651; 210/500.41; 210/500.36; 210/500.42; 210/600.23

(58) Field of Classification Search
CPC ...... B01D 61/147; B01D 71/68; B01D 11/04; B01D 61/00; B01D 69/08; B01D 71/44; C12M 1/12
USPC ............... 210/645, 650, 651, 500.27, 500.36, 210/500.41, 500.42; 435/69.1
See application file for complete search history.

(56) References Cited

U.S. PATENT DOCUMENTS 4,399,035 A * 8/1983 Nohmi et al. ............ 210/500.23
4,882,223 A * 11/1989 Aptel et al. .................. 428/398
(Continued)

FOREIGN PATENT DOCUMENTS

CN      1257434       6/2000
EP      0824960 A1    2/1998
(Continued)

OTHER PUBLICATIONS
European Search Report issued with respect to counterpart European Application No. 09816207.6, dated Nov. 27, 2012.
(Continued)

*Primary Examiner* — Ana Fortuna
(74) *Attorney, Agent, or Firm* — Greenblum & Bernstein, P.L.C.

(57) ABSTRACT

Use of a porous hollow fiber membrane for producing a clarified biomedical culture medium by a method including a filtration step of distributing a biomedical culture medium over the porous hollow fiber membrane, a tube wall of the hollow fiber membrane being constituted of a blend of a hydrophobic polymer and polyvinylpyrrolidone. A content of the polyvinylpyrrolidone is not lower than 0.2% by mass and not higher than 3% by mass relative to a total mass of the porous hollow fiber membrane, and, when the tube wall is divided in a membrane-thickness direction equally into three regions, a content of the polyvinylpyrrolidone in an outer circumferential region including an outer face is higher than a content of the polyvinylpyrrolidone in an inner circumferential region including an inner face, and an average pore size in the inner face is larger than an average pore size in the outer face.

13 Claims, 3 Drawing Sheets

(56) References Cited

U.S. PATENT DOCUMENTS

| | | | |
|---|---|---|---|
| 4,906,375 A * | 3/1990 | Heilmann | 210/500.23 |
| 5,340,480 A * | 8/1994 | Kawata et al. | 210/500.23 |
| 5,340,490 A * | 8/1994 | Decaire et al. | 252/67 |
| 5,436,068 A * | 7/1995 | Kobayashi et al. | 428/308.4 |
| 6,146,747 A * | 11/2000 | Wang et al. | 428/310.5 |
| 6,165,363 A | 12/2000 | Oishi et al. | |
| 6,432,309 B1 | 8/2002 | Fuke et al. | |
| 2004/0050791 A1 | 3/2004 | Herczeg | |
| 2007/0039868 A1 | 2/2007 | Ishibashi | |
| 2009/0057225 A1* | 3/2009 | Krause et al. | 210/650 |
| 2009/0280533 A1* | 11/2009 | Gorfien et al. | 435/69.1 |
| 2012/0111790 A1* | 5/2012 | Chidambaran et al. | 210/500.23 |

FOREIGN PATENT DOCUMENTS

| | | | |
|---|---|---|---|
| EP | 0 882 494 A1 | | 12/1998 |
| EP | 1 634 611 | | 3/2006 |
| EP | 1 875 957 A1 | | 1/2008 |
| JP | 60-22906 A | | 2/1985 |
| JP | 4-260419 A | | 9/1992 |
| JP | 5-76736 A | | 3/1993 |
| JP | 5-245350 A | | 9/1993 |
| JP | 7/155559 A | | 6/1995 |
| JP | 2004-525755 A | | 8/2004 |
| JP | 2005-88008 A | | 4/2005 |
| JP | 2005-220202 A | | 8/2005 |
| WO | 96/35504 A1 | | 11/1996 |
| WO | 97/22405 A1 | | 6/1997 |
| WO | 02/058828 A1 | | 8/2002 |
| WO | 2005/030375 A1 | | 4/2005 |
| WO | 2009/054495 A1 | | 4/2009 |

OTHER PUBLICATIONS

Chinese Office Action issued with respect to counterpart Chinese Application No. 200980137972.2, dated Jan. 23, 2013.
U.S. Appl. No. 13/063,021 to Satoshi Shiki, filed Mar. 9, 2011.
International Preliminary Report on Patentability and Written Opinion, mail date is May 10, 2011.
International Search Report, mail date is Nov. 17, 2009.
Notice of Allowance issued with respect to Japanese Application No. P2010-530874, mail date is Mar. 4, 2014.

* cited by examiner

USE OF POROUS HOLLOW-FIBER MEMBRANE FOR PRODUCING CLARIFIED BIOMEDICAL CULTURE MEDIUM

TECHNICAL FIELD

The present invention is related to the use of a porous hollow fiber membrane for producing a clarified biomedical culture medium.

BACKGROUND ART

Conventionally, as a method of removing microbial particles from a solution, a gel filtration method, a centrifugation method, an adsorption separation method, a precipitation method, a membrane filtration method, etc. are utilized. However, the gel filtration method is difficult to be industrially applied due to the facts that a target substance is diluted with the solvent used in gel filtration, the method is not suitable for large-scale processing, etc. The centrifugation method can only be applied in the case where the size of a microbial particle is not smaller than a few μm and the solution viscosity is low. The adsorption filtration method can be utilized for removal of a small amount of certain microbial particles, however, this method cannot be applied to a solution in which a variety of microorganisms are dispersed in a large amount. The precipitation method can be utilized in processing of a relatively large amount of solution, however, this method is not capable of completely removing microbial particles by itself.

On the other hand, the membrane filtration method utilizing a micro-filtration membrane or an ultrafiltration membrane is capable of removing any microorganism and, in addition, is capable of large-scale successive processing, thereby being suitable for industrial utilization.

However, as for conventional micro-filtration membranes and ultrafiltration membranes, there is a problem that a concentrated layer is formed from microorganisms removed on the surface of the membrane or the disrupted matters thereof and the surface of the membrane is blocked, so that an increase in filtration pressure and an over time decrease in filtration rate are likely to be caused.

To remove such a concentrated layer on the surface of the membrane, backwash may be performed by introducing a fluid opposite in the direction of filtration, however, a flow of a large amount of backwash fluid is required to wash off materials strongly adsorbing to the surface of the membrane, thereby filtration efficiency decreases.

In Patent Document 1, a hollow fiber membrane having a gradient structure with progressively decreasing pore sizes from the membrane inner surface toward the membrane outer surface and composed of polysulfone and polyvinylpyrrolidone is described. To obtain this hollow fiber membrane, polyvinylpyrrolidone of a relatively low molecular weight is used. In addition, removal of polyvinylpyrrolidone in the membrane on purpose from the hollow fiber membrane after membrane formation is described.

In Patent Document 2, a hollow fiber membrane which has a spongy structure throughout the membrane and has a dense layer with a thickness of 0.05 to 0.3 μm on at least one of the inner surface side and the outer surface side is described.

In addition, as cross-flow filtration or a filtration method utilizing countercurrent washing (backwash), for example, in Patent Document 3, a method of removing components that cause turbidity by performing backflushing for a short period of time is described. Furthermore, in Patent Document 4, a method of removing turbidity in which dead-end filtration and backwash for a short period of time are combined is described.

CITATION LIST

Patent Literature

[Patent Document 1] International Publication No. 2002/58828 pamphlet
[Patent Document 2] International Publication No. 1996/35504 pamphlet
[Patent Document 3] Japanese Patent Application Laid-Open Publication No. Hei-7-155559
[Patent Document 4] Japanese Patent Application Laid-Open Publication No. Hei-4-260419

SUMMARY OF INVENTION

Technical Problem

However, in cross-flow filtration using a conventional hollow fiber membrane, it is required to increase the flow rate of a processing solution to prevent a blockage of the surface of the membrane and, by increasing the flow rate, disruption, deformation, etc. of microbial particles become more likely to take place. In the case where microbial particles are disrupted, there is a problem that the disrupted matters pass through the hollow fiber membrane and contaminate a clarified biomedical culture medium. In addition, in the case where a conventional hollow fiber membrane is used, there is a problem that, at the time of removing to-be-removed materials accumulated on the surface of the membrane by countercurrent washing, a flow of a large amount of backwash fluid is required in order to remove the to-be-removed materials strongly adsorbing to the surface of the membrane, thereby processing efficiency decreases.

Conventionally, in order to industrially obtain clarified or turbidity-removed permeate from a biomedical culture medium, there was no other choice but to employ a method of clarifying a culture medium in two steps, namely separating cells with a centrifuge and then filtrating off impurities such as disrupted cell products with a membrane.

In Patent Document 1, applying a hollow fiber membrane for a biomedicine is described, however, clarification of a biomedical culture medium is not clearly described. In addition, in Patent Document 2, there is no description related to the molecular weight of polyvinylpyrrolidone that forms a hollow fiber membrane and a polyvinylpyrrolidone content in the membrane. Furthermore, in Patent Document 2, there is no description related to using a hollow fiber membrane in an application to a biomedical culture medium.

In the methods described in Patent Document 3, a washing effect is not sufficient and, in the case of performing processes successively, an increase in filtration pressure takes place. In addition, in the methods described in Patent Document 4, though the permeate flow rate itself during filtration can be increased, switching between filtration and backwash is frequently performed to decrease overall efficiency of turbidity removing operation, and therefore the methods are not suitable for industrial utilization.

An object of the present invention is to efficiently produce a sufficiently clarified biomedical culture medium in which a contamination of disrupted matters such as cells is small.

Solution to Problem

That is to say, the present invention is related to the following use of a porous hollow fiber membrane for producing a clarified biomedical culture medium.

(1) Use of a porous hollow fiber membrane a tube wall of which is constituted of a blend of a hydrophobic polymer and polyvinylpyrrolidone, for producing a clarified biomedical culture medium by a method including a filtration step (an inside-out filtration step) of distributing a biomedical culture medium over the porous hollow fiber membrane. A polyvinylpyrrolidone content in the porous hollow fiber membrane is not lower than 0.2% by mass and not higher than 3% by mass relative to a total mass of the porous hollow fiber membrane. When the tube wall of the porous hollow fiber membrane is divided in the membrane-thickness direction equally into three regions, a polyvinylpyrrolidone content in an outer circumferential region including an outer face is higher than a polyvinylpyrrolidone content in an inner circumferential region including an inner face. An average pore size in the inner face of the porous hollow fiber membrane is larger than an average pore size in the outer face.

(2) The use according to (1), in which a weight average molecular weight of polyvinylporrolidone is not lower than 400000 and not higher than 800000.

(3) The use according to (1) or (2), in which the porous hollow fiber membrane has the average pore size in the inner face is not smaller than 1 μm and not larger than 50 μm, the outer circumferential region has a rejection pore size of not smaller than 0.1 μm but smaller than 1 μm, and a membrane thickness of the tube wall is not smaller than 300 μm and not larger than 1000 μm.

(4) The use according to any one of (1) to (3), in which the porous hollow fiber membrane satisfies the following formula (I):

$$C_{out}/C_{in} \geq 2 \qquad (I)$$

[in the formula (I), $C_{out}$ represents a hydrophilic polymer content in the outer circumferential region, and $C_{in}$ represents a hydrophilic polymer content in the inner circumferential region].

(5) The use according to any one of (1) to (4), in which the porous hollow fiber membrane has an inner diameter of not smaller than 1000 μm and not larger than 2000 μm.

(6) The use according to any one of (1) to (5), in which the hydrophobic polymer is polysulfone.

(7) The use according to any one of (1) to (6), in which the inside-out filtration is performed by cross-flow filtration including, while feeding the biomedical culture medium through one fiber end of the porous hollow fiber membrane, discharging the biomedical culture medium filtrated and clarified, and draining the biomedical culture medium left unfiltered in which a suspended substance is concentrated through the other fiber end of the porous hollow fiber membrane, and a feeding speed of the biomedical culture medium is not lower than 0.2 m/sec and not higher than 1.0 m/sec as a linear speed.

(8) The use according to any one of (1) to (7), further including a step of countercurrently washing the porous hollow fiber membrane by using permeate obtained in the step of performing inside-out filtration.

(9) The use according to any one of (1) to (8), in which the porous hollow fiber membrane is a porous hollow fiber membrane treated by steam sterilization.

(10) The use according to any one of (1) to (6), in which the method including the filtration step of distributing a biomedical culture medium over the porous hollow fiber membrane is a method of clarifying the biomedical culture medium by using a hollow fiber membrane module comprising: a housing having openings at both ends: a hollow fiber membrane bundle having a plurality of the porous hollow fiber membrane, the bundle being carried inside the housing, one end of the bundle being immobilized at a side of one of the openings and the other end of the bundle being immobilized at a side of the other of the openings, so as to make it possible for the biomedical culture medium that is a fluid to be filtrated to flow inwards or outwards through the openings of the housing; a first nozzle provided on a side face of the housing in the vicinity of one end thereof and allowing a permeation fluid that is the fluid to be filtrated and filtrated through the porous hollow fiber membrane to flow inwards or outwards therethrough; a second nozzle provided on a side face of the housing in the vicinity of the other end thereof and allowing the permeation fluid to flow inwards or outwards therethrough. While disposing the hollow fiber membrane module in such a way that one of the first nozzle and the second nozzle is higher than the other, a filtration step of performing filtration by distributing the fluid to be filtrated over an interior of a tube of the hollow fiber membrane; and a backwash step of filling a space between the porous hollow fiber membrane and the housing with a backwash fluid and introducing gas into an interior of the housing through the nozzle at a higher position to gradually lower a fluid level of the backwash fluid, washing the porous hollow fiber membrane with the backwash fluid, and draining backwash waste through the opening at an upper side, are carried out alternately.

(11) The use according to (10), in which the filtration step is a cross-flow filtration step of, while feeding the fluid to be filtrated through one fiber end of the porous hollow fiber membrane, discharging the fluid to be filtrated that is filtrated and clarified, and draining the fluid to be filtrated left unfiltered in which a suspended substance is concentrated through the other fiber end of the porous hollow fiber membrane.

Advantageous Effects of Invention

According to the present invention, it is possible to efficiently produce a sufficiently clarified biomedical culture medium in which a contamination of disrupted matters such as cells is small. According to the present invention, there is no need to perform purification (clarification) of a biomedical culture medium in two steps, namely cell separation by centrifugation and subsequent filtration, and sufficient clarification is possible by filtration alone with a membrane.

According to the present invention, it is possible to provide a production method of a clarified biomedical culture medium, including an inside-out filtration step capable of maintaining a high filtration rate for a prolonged period of time in which cell destruction and deformation are low, washing the membrane is easy, and processing efficiency is high, compared to a filtration method using a conventional porous hollow fiber membrane, the method being excellent in production efficiency and being capable of producing a sufficiently clarified biomedical culture medium in which a contamination of disrupted matters such as cells is small.

DESCRIPTION OF EMBODIMENTS

Figure 1:
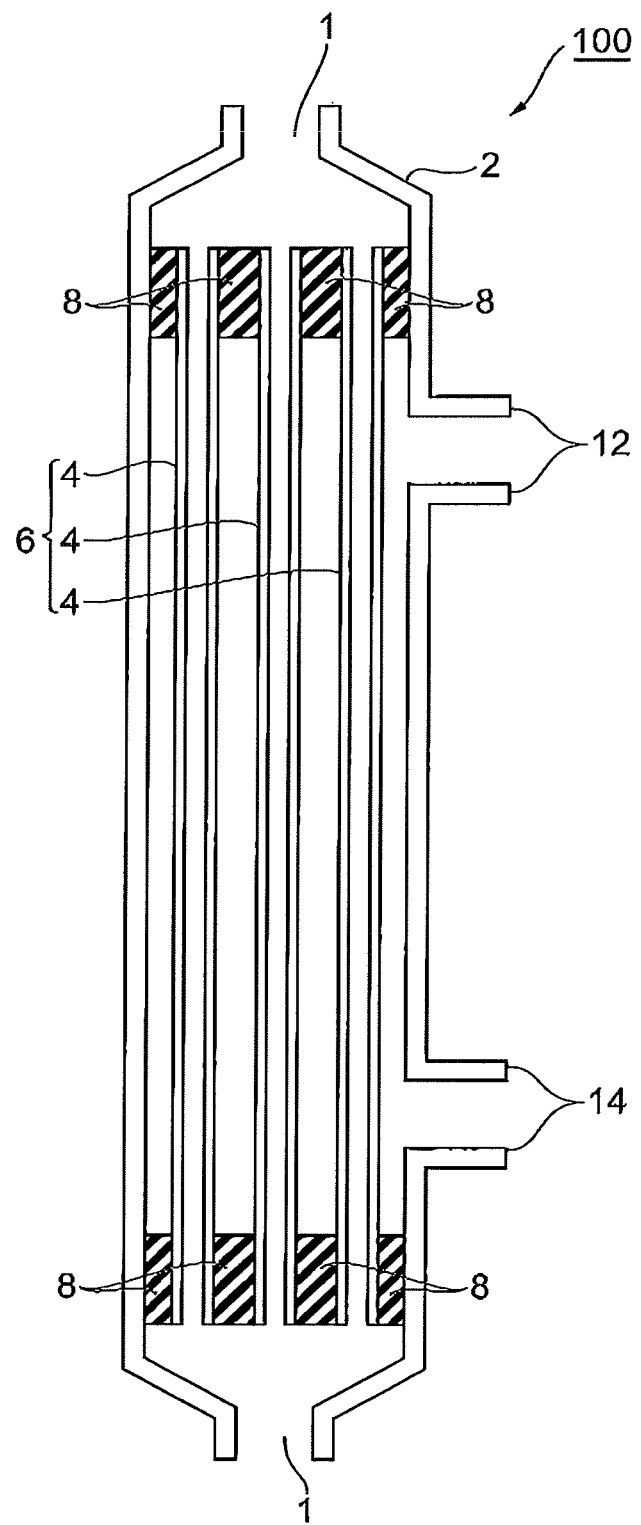
[FIG. 1] A cross sectional view in schematic form showing a hollow fiber membrane module.

In the following, suitable embodiments of the present invention will be described in detail.

A production method of a clarified or turbidity-removed biomedical culture medium in which the porous hollow fiber membrane according to this embodiment is used (hereinafter, may be simply referred to as "a clarification method") includes an inside-out filtration step of distributing a biomedical culture medium over the porous hollow fiber membrane a tube wall of which is constituted of a blend of a hydrophobic polymer and polyvinylpyrrolidone.

The biomedical culture medium is a culture medium for producing recombinant proteins by a cell culture using, for example, a host cell containing a Chinese hamster ovary (CHO) cell. The biomedical culture medium is not limited to that as long as containing a target protein, and may be plasma, serum, an ascites fluid, or a product obtained by subjecting those to various purification treatments, for example.

The culture medium contains impurities as a suspended matter. In addition, the culture medium contains a lot of impurity proteins other than the target protein. That is to say, the culture medium is a fluid containing dissolution products of impurity proteins and impurities that is a suspended matter. Furthermore, bacteria, etc. may also be contained in the culture medium. Examples of the impurity existing as a suspended matter and the impurity protein include, but not limited to, cell debris such as cell walls and disrupted cell products, host cell proteins (HCPs), nucleic acids, endotoxins, etc.

The porous hollow fiber membrane is a porous hollow fiber membrane in which, when the tube wall is divided in the membrane-thickness direction equally into three regions, the hydrophilic polymer content in an outer circumferential region including the outer face is higher than the hydrophilic polymer content in an inner circumferential region including the inner face, and the average pore size in the inner face is larger than the average pore size in the outer face.

In order to divide the tube wall in the membrane-thickness direction equally into three regions, for example, a part of the tube wall (that indicates a side wall constituting the porous hollow fiber membrane having a hollow annular form) of the porous hollow fiber membrane may be cut out to obtain a film-like piece of the tube wall, and the piece may be equally sliced into three pieces in the membrane-thickness direction. In this case, the region having a thickness of one-third and including the outer face is referred to as "the outer circumferential region", and the region having a thickness of one-third and including the inner face is referred to as "the inner circumferential region". Meanwhile, the central part can be referred to as "the central region".

Preferably, the hydrophilic polymer content in the outer circumferential region is the highest, followed in order by those in the central region and the inner circumferential region. The porous hollow fiber membrane as above is, in the inner circumferential region thereof through which the culture medium passes first, likely to adsorb to-be-removed materials and excellent in filtration performance due to a relatively low hydrophilic polymer content thereof. On the other hand, in the outer circumferential region through which the culture medium passes lastly, the porous hollow fiber membrane can prevent deposition of to-be-removed materials and a blockage of membrane pores accompanied therewith due to a relatively high hydrophilic polymer content thereof. In the central region between these two, the porous hollow fiber membrane has both of the features in a good balance. Thus, a porous hollow fiber membrane having the above-mentioned configurations is further excellent in filtration performance, is less prone to cause a blockage of membrane pores, and can maintain a high filtration rate for a further prolonged period of time.

The porous hollow fiber membrane preferably satisfies the following formula (A).

$$P_a < P_b < P_c \tag{A}$$

In the formula (A), $P_a$ represents the average pore size in a cross section of the outer circumferential region, $P_b$ represents the average pore size in a cross section of the central region, and $P_c$ represents the average pore size in a cross section of the inner circumferential region.

The porous hollow fiber membrane as above can reject, in the inner circumferential region, the to-be-removed materials that the inner face cannot reject, can remove, in the central region, the to-be-removed materials that even the inner circumferential region cannot reject, and can reject, in the outer circumferential region, the to-be-removed materials that even the central region cannot reject. That is to say, the porous membrane as above rejects to-be-removed materials in multiple stages and therefore is further excellent in fractionation performance.

The hydrophobic polymer denotes a polymer having a critical surface tension ($\gamma c$) at 20° C. of not lower than 50 nN/m, and the hydrophilic polymer denotes a polymer having a critical surface tension ($\gamma c$) at 20° C. of lower than 50 nN/m. In addition, the average pore size can be calculated by observing the inner face or the outer face with an electron microscope at a magnification in which not less than 10 pores can be observed per one field of view, applying circle approximation to the pores in the obtained microscope photograph, and determining the diameter using the area average value. The blend of a hydrophobic polymer and a hydrophilic polymer means a mixture that contains both a hydrophobic polymer and a hydrophilic polymer and is in any phase structure (for example, whether the structure presents compatible phases or phase separation does not matter, but preferably the structure is not fully compatible).

The porous hollow fiber membrane is a membrane having a hollow annular form, and this form makes it possible to increase the membrane area per module unit volume, compared to a flat membrane.

In the porous hollow fiber membrane, the hydrophilic polymer content in the outer circumferential region including the outer face is higher than the hydrophilic polymer content in the inner circumferential region including the inner face, and the average pore size in the inner face is larger than the average pore size in the outer face. With the above-mentioned configurations, compared to a conventional porous hollow fiber membrane, the porous hollow fiber membrane has high strength that withstands a change in temperature and a change in pressure, can maintain both the filtration rate and the fractionation property, makes to-be-removed materials less prone to accumulate on the surface of the membrane and in the interior of the membrane, makes a blockage of membrane pores less prone to take place, can maintain a high filtration rate for a prolonged period of time, and can be easily washed by a known hollow fiber membrane washing method. Examples of the washing method include, for example, countercurrent washing of feeding a cleaning solution from the outer face, air scrubbing of introducing air bubbles into a module to make a membrane swayed thereby removing sediment, etc.

With the above-mentioned configurations, the porous hollow fiber membrane, in the inner circumferential region, can fully exert a depth filtration effect of holding particles smaller than the membrane pore in the interior of the membrane to remove them. On the other hand, in the outer circumferential region in which the hydrophilic polymer content is high and adsorption of particles to the membrane is low, thereby a blockage of membrane pores caused by adsorption of particles can be prevented. By preventing a blockage of membrane pores caused by adsorption of particles to the outer circumferential region in which pore sizes are small, a high filtration rate can be maintained for a prolonged period of time. In addition, since being capable of fully exerting the depth filtration effect in the inner circumferential region in which pore sizes are large, the porous hollow fiber membrane is excellent in filtration performance such as fractionation property.

Examples of the hydrophilic polymer include, for example, polyvinylpyrrolidone, polyethylene glycol, polyvinyl alcohol, celluloses, and the derivative substances thereof, etc. Among them, as the hydrophilic polymer, polyvinylpyrrolidone is preferable. These hydrophilic polymers can be used alone or as a mixture of two or more of these. These hydrophilic polymers are excellent in compatibility with a hydrophobic polymer, and made into a porous hollow fiber membrane that is uniform and excellent in mechanical strength. In addition, they make it possible to further prevent adsorption of to-be-removed materials to the surface of the membrane and the interior of the membrane, and make washing easy.

Examples of the hydrophobic polymer include, for example, polysulfone, polyvinylidene fluoride, polyvinylidene chloride, polyvinyl chloride, etc. Among them, as the hydrophobic polymer, polysulfone and polyvinylidene fluoride are preferable. These hydrophobic polymers can be used alone or as a mixture of two or more of these. With these hydrophobic polymers, the porous hollow fiber membrane is further excellent in strength against a change in temperature and a change in pressure and can express high filtration performance.

The average pore size in the inner face is preferably not smaller than 1 μm and not larger than 50 μm, more preferably not smaller than 5 μm and not larger than 40 μm, and further more preferably not smaller than 10 μm and not larger than 30 μm. In the case where the average pore size in the inner face is smaller than 1 μm, it is impossible to fully obtain the depth filtration effect of holding to-be-removed materials in the interior of the membrane, and a blockage of membrane pores caused by deposition of to-be-removed materials on the surface of the membrane may be likely to take place. In addition, in the case where the average pore size in the inner face is larger than 50 μm, the ratio of pores on the surface of the membrane is high and therefore strength of the porous hollow fiber membrane tends to decrease. Meanwhile, in order to make the average pore size in the inner face fall within the above-mentioned range, in the production method to be described below, for example, the concentration of a good solvent in an inner congealing fluid may be not lower than 85% by weight.

The average pore size in the outer face is preferably not smaller than 0.1 μm and not larger than 20 μm, more preferably not smaller than 0.2 μm and not larger than 15 μm, and further more preferably not smaller than 0.3 μm and not larger than 10 μm. Meanwhile, in order to make the average pore size in the outer face fall within the above-mentioned range, in the production method to be described below, for example, the temperature of an outer congealing fluid may be from 50° C. to 90° C.

The outer circumferential region preferably has a rejection pore size of not smaller than 0.05 μm but smaller than 1 μm, further more preferably has a rejection pore size of not smaller than 0.1 μm but smaller than 1 μm, and more preferably has a rejection pore size of not smaller than 0.2 μm and not larger than 0.8 μm. In the case where the rejection pore size is smaller than 0.05 μm, permeation resistance may increase, the pressure required for filtration may increase, and a blockage at the surface of the membrane caused by destruction and deformation of microbial particles, a decrease in filtration efficiency, etc. may take place. In addition, in the case of not smaller than 1 μm, a sufficient fractionation property is less prone to be obtained. Meanwhile, in order to make the rejection pore size in the outer circumferential region fall within the above-mentioned range, in the production method to be described below, for example, for example, the temperature of an outer congealing fluid may be from 50° C. to 90° C.

The rejection pore size herein means the pore size of a particle at which the rejected-permeation rate of the particle is 90% at the time of filtration of, using the porous hollow fiber membrane, particle dispersion in which particles of a certain pore size are dispersed. Specifically, for example, filtration of particle dispersion is performed to measure a change in concentration of the particle before and after filtration. By performing this measurement while the particle size is changed by about 0.1 μm starting from 0.1 μm, a rejection curve for the particle is created. The rejection curve for the particle size that can achieve a 90% rejection can be read out, and the size can be referred to as the rejection pore size.

The porous hollow fiber membrane preferably contains the minimum pore size-layer in the outer circumferential region. When the minimum pore size-layer exists in the outer circumferential region in which the hydrophilic polymer content is high, it is possible to prevent more certainly a blockage of membrane pores caused by adsorption of particles. Meanwhile, the minimum pore size-layer herein indicates a layer that contains the minimum pore size on observation of a cross section of the membrane with an electron microscope. The pore size in the minimum pore size-layer is almost the same as the rejection pore size, and the pore size in the minimum pore size-layer can be obtained from a measurement of the rejection pore size. The pore size in the minimum pore size-layer is preferably not smaller than 0.05 μm but smaller than 1 μm, more preferably not smaller than 0.1 μm but smaller than 1 μm, and further more preferably not smaller than 0.2 μm and not larger than 0.8 μm. Meanwhile, in order to make the outer circumferential region contain the minimum pore size-layer, in the production method to be described below, for example, the concentration of a good solvent in an inner congealing fluid may be not lower than 85% by weight, and the concentration of a good solvent in an outer congealing fluid may be not higher than 50% by weight.

The porous hollow fiber membrane preferably has a gradient structure in which the pore size successively decreases from the inner face toward the minimum pore size-layer. With the configuration as above, it is possible to obtain more of the depth filtration effect of holding to-be-removed materials in the interior of the membrane, and to maintain a high filtration rate for a more prolonged period of time. Meanwhile, in order to make the pore size successively decrease from the inner face toward the minimum pore size-layer, in the production method to be described below, for example, the concentration of a good solvent in an inner congealing fluid may be not lower than 85% by weight, and the concentration of a good solvent in an outer congealing fluid may be not higher than 50% by weight.

In the porous hollow fiber membrane, the membrane thickness is preferably not smaller than 300 μm and not larger than 1000 μm, and more preferably not smaller than 350 μm and not larger than 800 μm. In a porous hollow fiber membrane with a membrane thickness of smaller than 300 μm, a range, in the interior of the membrane, that can hold to-be-removed materials is limited, and therefore the depth filtration effect may not be fully obtained and a decrease in the filtration rate tends to be likely to take place. In a porous hollow fiber membrane with a membrane thickness of larger than 1000 μm, it is difficult to wash off the to-be-removed materials deposited in the interior of the membrane and filtration performance may not fully recover after washing. Meanwhile, in order to make the membrane thickness fall within the above-mentioned range, in the production method to be described below, for example, an outside channel of a double tubular nozzle may be 200 μm to 1200 μm (preferably 300 μm to 1000 μm).

In the porous hollow fiber membrane, the hydrophilic polymer content is preferably not lower than 0.2% by mass and not higher than 3% by mass, and more preferably not lower than 0.5% by mass and not higher than 2% by mass, relative to the total mass of the porous hollow fiber membrane. In a porous hollow fiber membrane with a hydrophilic polymer content of lower than 0.2% by mass, to-be-removed materials are likely to adsorb to the surface of the membrane and the interior of the membrane, a blockage of membrane pores is likely to take place, and washing thereof tends to be difficult. In a porous hollow fiber membrane with a hydrophilic polymer content of higher than 3% by mass, membrane pores may be blocked due to swelling of hydrophilic polymers and permeation resistance may increase. In addition, with a hydrophilic polymer content of within the above-mentioned range, washing performance is excellent and it is possible to maintain high filtration performance even in the case of repeated filtration and washing. Meanwhile, in order to make the hydrophilic polymer content fall within the above-mentioned range, in the production method to be described below, for example, the proportion of hydrophobic polymer to hydrophilic polymer in the blend of a hydrophobic polymer and a hydrophilic polymer may be the former:the latter=(1):(0.1 to 1.5) (preferably, the former:the latter=(1):(0.5 to 1.3)).

The porous hollow fiber membrane preferably satisfies the following formula (I).

$$C_{out}/C_{in} \geq 2 \qquad (I)$$

In the above formula (I), $C_{out}$ represents the hydrophilic polymer content in the outer circumferential region, and $C_{in}$ represents the hydrophilic polymer content in the inner circumferential region. A porous hollow fiber membrane in which hydrophilic polymers present the distribution as above is further excellent in the depth filtration effect in the inner circumferential region and in a preventing effect of a blockage of membrane pores caused by adsorption of to-be-removed materials to the outer circumferential region. In addition, washing performance is excellent and it is possible to maintain high filtration performance even in the case of repeated filtration and washing. Meanwhile, in order to satisfy the following formula (I), in the production method to be described below, for example, the proportion of hydrophobic polymer to hydrophilic polymer in the blend of a hydrophobic polymer and a hydrophilic polymer may be the former:the latter=(1):(0.1 to 1.5) (preferably, the former:the latter=(1):(0.3 to 1.2)).

In the porous hollow fiber membrane, the inner diameter is preferably not smaller than 1000 μm and not larger than 2000 μm. When the inner diameter is smaller than 1000 μm, in the case of filtrating off suspended substances that are likely to aggregate, such as microbial particles, etc., an inlet into a hollow fiber may be blocked with the aggregated suspended substances, so that filtration may not be able to be continued. In addition, in the case where the inner diameter is larger than 2000 μm, each piece of the porous hollow fiber membranes tends to be thick, the effective membrane area per module tends to decrease, and filtration performance tends to decrease. Meanwhile, in order to make the membrane thickness fall within the above-mentioned range, in the production method to be described below, for example, the diameter of an inside channel of the double tubular nozzle may be 500 μm to 2500 μm (preferably, 600 μm to 2200 μm).

The porous hollow fiber membrane may be sterilized in an autoclave process. By being sterilized in an autoclave process, the porous hollow fiber membrane can be suitably used for filtration of biomedical culture mediums, etc. In the case of performing an autoclave process, a hydrophobic polymer in which a change in water permeability is small before and after the autoclave process is preferable. Specifically, the rate of change in water permeation amount ($F_{AC}/F_0$) before and after the autoclave process, being determined from the deionized water permeation amount ($F_0$) before the autoclave process and the deionized water permeation amount ($F_{AC}$) after the process, is preferably not lower than 0.9 but lower than 1.1. Examples of such a hydrophobic polymer include polysulfone, for example.

Hereinafter, a production method of the porous hollow fiber membrane will be described in detail.

The production method of the porous hollow fiber membrane includes a coagulation step of performing the following discharges (extrusions) (1) and (2) simultaneously for coagulation in the outer congealing fluid:

(1) discharging the inner congealing fluid through the inside channel of the double tubular nozzle, (2) discharging, through the outside channel of the double tubular nozzle, a raw fluid containing a hydrophobic polymer, a hydrophilic polymer, a good solvent for both of the polymers, and a non-solvent for the hydrophobic polymer.

With the production method as above, the porous hollow fiber membrane can be easily obtained. Meanwhile, after the discharges (extrusions) (1) and (2) and before coagulation in the outer congealing fluid, allowing the raw fluid to pass through an airflow part is preferable. "To pass through an airflow part" herein indicates allowing the raw fluid to temporarily pass through air (or through gas such as an inert gas) so that the raw fluid discharged through the double tubular nozzle does not readily contact with the outer congealing fluid.

The double tubular nozzle herein indicates a nozzle in which an inside channel is formed at an central part of the nozzle, an outside channel is formed so as to surround that, and a partition is formed between both channels. As for the inside channel of the double tubular nozzle, the cross section thereof at right angles to the length direction of the nozzle is preferably circular, as for the outside channel of the double tubular nozzle, the cross section thereof at right angles to the length direction of the nozzle is preferably annular, and both channels are preferably concentric (having a common axis).

As the inner congealing fluid, an aqueous solution containing a good solvent for the hydrophobic polymer at not lower than 80% by weight but lower than 100% by weight relative to the total mass of the inner congealing fluid is preferable. In addition, from the viewpoint of obtaining a porous hollow fiber membrane with a pore size in the inner face of not smaller than 5 μm, an aqueous solution containing that at not lower than 85% by weight but lower than 98% by weight is preferable. The temperature of the inner congealing fluid preferably falls within the range of −30 to +30° C. relative to the temperature at which the raw fluid is discharged through the double tubular nozzle so as to decrease a change in performance due to an inconsistent temperature of the fluid.

As the outer congealing fluid, a coagulation fluid coagulability of which to the raw fluid is higher than that of the inner congealing fluid and the main component of which is water is preferable. With the outer congealing fluid as above, it is possible to obtain a porous hollow fiber membrane in which the pore size in the inner face is larger than the pore size in the outer face and the pore size successively decreases from the inner face toward the minimum pore size-layer. Coagulability can be measured by casting a transparent raw fluid for membrane production onto glass thinly and thereonto dropping a coagulation fluid for each to get the turbidity generating rate, and a coagulation fluid that is high in the turbidity generating rate is a fluid having a high coagulating power. The temperature of the outer congealing fluid is preferably not lower than 30° C. and not higher than 90° C., and more preferably not lower than 50° C. and not higher than 85° C.

The good solvent for both of the hydrophobic polymer and the hydrophilic polymer indicates a solvent in which insoluble components are not observed when 30 g of the hydrophobic polymer or the hydrophilic polymer is dissolved in 100 g of solvent. As the good solvent that dissolves both of the polymers, from the viewpoint of stability of the raw fluid, a solvent that contains not lower than 80% of a mixed solvent consisting of one or two or more species selected from N-methylpyrrolidone (NMP), dimethylformamide (DMF), and dimethylacetamide (DMAC) is preferable, and a solvent that contains not lower than 90% of that is more preferable. In addition, from the viewpoint of obtaining ease of handling and high water permeability, the good solvent preferably contains N-methylpyrrolidone.

The content of the good solvent for both of the hydrophobic polymer and the hydrophilic polymer in the raw fluid is preferably not lower than 40% by mass and not higher than 75% by mass, and more preferably not lower than 50% by mass and not higher than 70% by mass, relative to the total mass of the raw fluid.

The non-solvent for the hydrophobic polymer indicates a solvent in which insoluble components are observed when 5 g of the hydrophobic polymer is dissolved in 100 g of solvent. Examples of the non-solvent for the hydrophobic polymer include water, alcohol compounds, etc. Among them, from the viewpoints of ease of an adjustment of the raw fluid for membrane production, a less tendency to cause a change in composition during storage, ease of handling, etc., glycerol is preferable.

The non-solvent content in the raw fluid is preferably not lower than 0.5% by mass and not higher than 15% by mass, and more preferably not lower than 1% by mass and not higher than 10% by mass, relative to the total mass of the raw fluid.

As for the raw fluid, the solution viscosity thereof at the temperature that the raw fluid is discharged through the double tubular nozzle is preferably not lower than 30 Pa·sec and not higher than 200 Pa·sec, and more preferably not lower than 40 Pa·sec and not higher than 150 Pa·sec. In the case where the solution viscosity is lower than 30 Pa·sec, the raw fluid for membrane production that is discharged through the outside channel of the double tubular nozzle drops under its own weight to make it difficult to have the airflow time long enough, and to make it difficult to produce a porous hollow fiber membrane with a thickness of not smaller than 300 μm and a pore size of not smaller than 0.1 μm. In addition, in the case where the solution viscosity is larger than 200 Pa·sec, consistent extrusion through the double tubular nozzle is difficult and unevenness in membrane performance may take place.

In the above-mentioned production method, the hydrophilic polymer is preferably polyvinylpyrrolidone with a weight average molecular weight of not lower than 400000 and not higher than 800000. With the hydrophilic polymer as above, it is possible to easily adjust a raw fluid with a solution viscosity of within the above-mentioned suitable range.

The hydrophilic polymer content in the raw fluid is preferably not lower than 8% by mass and not higher than 30% by mass, and more preferably not lower than 10% by mass and not higher than 25% by mass, relative to the total mass of the raw fluid. In addition, the hydrophobic polymer content in the raw fluid is preferably not lower than 15% by mass and not higher than 30% by mass, and more preferably not lower than 18% by mass but not lower than 25% by mass, relative to the total mass of the raw fluid. In the case where the hydrophilic polymer and hydrophobic polymer contents fall within the above-mentioned ranges, it is possible to easily adjust a raw fluid with a solution viscosity of within the above-mentioned suitable rang; and it is possible to obtain a porous hollow fiber membrane with a hydrophilic polymer content of within the above-mentioned suitable range.

In the above-mentioned production method, it is preferable to remove part of hydrophilic polymers using an aqueous solution containing an oxidizing agent at the same time as or after the coagulation step (preferably after the coagulation step). Examples of the aqueous solution containing an oxidizing agent include, for example, an aqueous solution of sodium hypochlorite, an aqueous solution of hydrogen peroxide, etc. With the production method as above, it is possible to obtain a porous hollow fiber membrane with a hydrophilic polymer content of within the above-mentioned suitable range and further excellent in filtration performance and washing performance. In the case of using the aqueous solution of sodium hypochlorite as the aqueous solution containing an oxidizing agent, the aqueous solution with a concentration of not lower than 100 ppm and not higher than 50000 ppm may be used, and it is possible to adjust a decomposition time and temperature depending on a species, a content, etc. of the hydrophilic polymers to be used. In addition, the oxidizing agent that is used is preferably washed off afterwards using water, etc.

The production method of a clarified biomedical culture medium according to this embodiment (hereinafter, may be referred to as "a clarification method") includes the inside-out filtration step of distributing the biomedical culture medium over the above-mentioned porous hollow fiber membrane. With the above-mentioned configurations, the production method according to this embodiment is excellent in production efficiency and makes it possible to produce a biomedical culture medium low in a contamination of disrupted matters such as cells and fully clarified or turbidity-removed.

Compared to a method using a conventional hollow fiber membrane, the above-mentioned inside-out filtration step makes it possible to maintain a high filtration rate for a prolonged period of time, is low in cell destruction and deformation, makes it easy to wash the membrane, and is excellent in processing efficiency.

The inside-out filtration is preferably cross-flow filtration. The cross-flow filtration indicates a filtration method of introducing the biomedical culture medium through one end of the porous hollow fiber membrane into the interior of the tube for feeding the medium along the tube wall, discharging the biomedical culture medium clarified or turbidity-removed through pores by filtration through the tube wall, and draining the biomedical culture medium concentrated by filtration through the other end of the porous hollow fiber membrane. In the cross-flow filtration, the feeding speed is preferably not lower than 0.2 m/sec and not higher than 1.0 m/sec as a linear speed. In the case where the feeding speed is lower than 0.2 m/sec, the filtration rate may decrease, and in the case of higher than 1.0 m/sec, cells contained in the biomedical culture medium may be disrupted and the disrupted matters may contaminate permeate. The linear speed herein is a linear speed at the time of passage through an inner diameter part of the membrane, and is possible to be calculated from the feeding flow rate (ml/sec) and the inner diameter of the membrane.

The clarification method (a method of removing turbidity) preferably further includes a step of countercurrently washing the porous hollow fiber membrane using the permeate obtained in the step of performing inside-out filtration. By regularly removing sediment on the surface and in the interior of the porous hollow fiber membrane with countercurrent washing, it is possible to maintain filtration performance of the porous hollow fiber membrane for a prolonged period of time. Since it is possible to maintain a sufficient filtration rate for a prolonged period of time with a low pressure and a low feeding speed, it is possible to further prevent disruption of cells contained in the biomedical culture medium.

The porous hollow fiber membrane is preferably a porous hollow fiber membrane treated with steam sterilization. By sterilizing the porous hollow fiber membrane with steam sterilization, it is possible to prevent a contamination of bacteria, etc. in permeate.

It is possible to perform steam sterilization by, for example, steam heating the porous hollow fiber membrane at 120 to 135° C.

Hereinafter, with reference to drawings, a suitable embodiment of the hollow fiber membrane module and the clarification method using the same will be described. Meanwhile, identical components are provided with the same symbols in the description of the drawings, and a duplicating description is omitted. In addition, parts of the drawings are exaggerated so as to make understanding easier, and sizes and proportions are not necessarily the same as those in the description.

FIG. 1 is a cross sectional view in schematic form showing the hollow fiber membrane module to be used in the clarification method according to the embodiment. A hollow fiber membrane module 100 shown in FIG. 1 comprises a housing 2 having openings 1 at both ends, a hollow fiber membrane bundle 6 including a plurality of hollow fiber membranes 4 carried inside the housing 2, a first nozzle 12 provided on a side face of the housing 2 in the vicinity of one end thereof, and a second nozzle 14 provided on a side face of the housing 2 in the vicinity of the other end thereof. As the hollow fiber membrane 4, the porous hollow fiber membrane according to the above-mentioned embodiment is suitably used.

Within the hollow fiber membrane module 100, in order that a fluid to be filtrated can flow inwards or outwards through the openings 1 of the housing 2, one end of the hollow fiber membrane bundle 6 is liquid tightly immobilized at the side of one opening 1 and the other end thereof is liquid tightly immobilized at the side of the other one opening 1 respectively with an immobilizing member 8.

The clarification method according to the embodiment is a method in which a filtration step of performing filtration by distributing the fluid to be filtrated over the interior of a tube of the above-mentioned hollow fiber membrane, and a backwash step of filling the space between the hollow fiber membrane and the housing with a backwash fluid and introducing gas into the interior of the housing through the nozzle at the higher position thereby gradually lowering the fluid level of the backwash fluid, washing the hollow fiber membrane with the backwash fluid, and draining backwash waste through the upper opening are alternately carried out.

Figure 2:
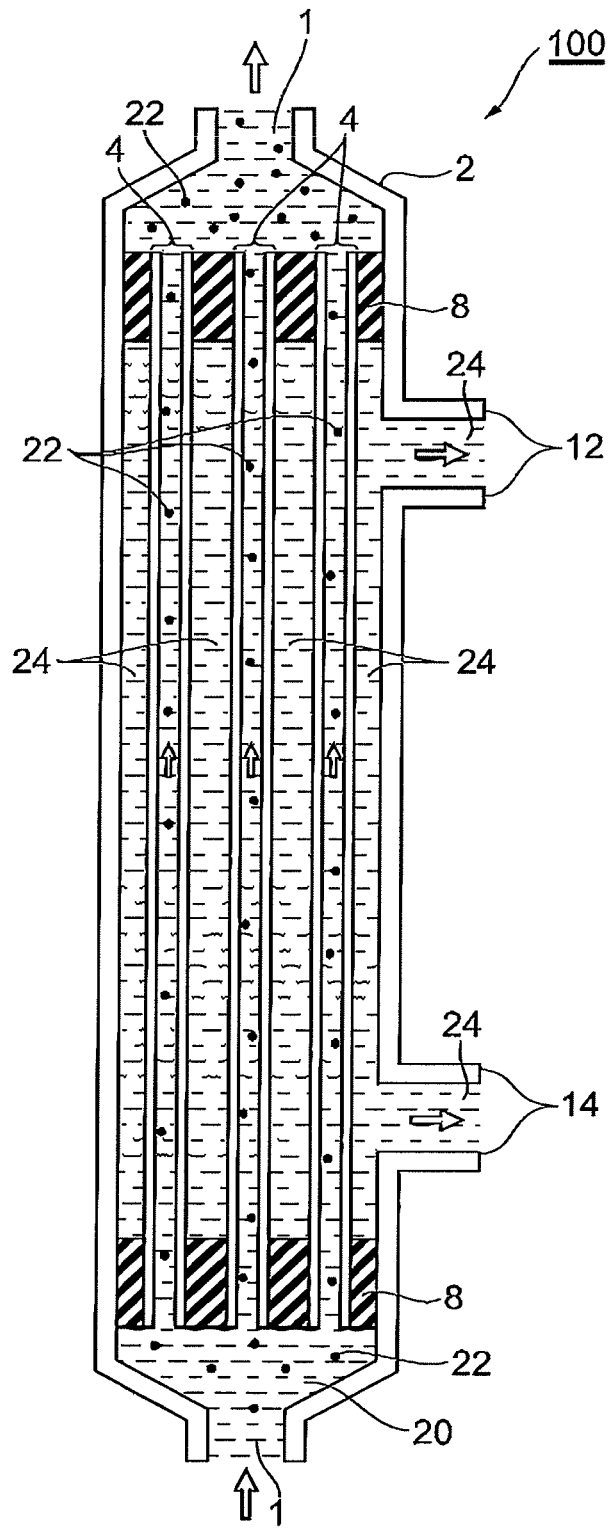
[FIG. 2] A cross sectional view in schematic form showing filtration using the hollow fiber membrane module of FIG. 1.

With reference to FIG. 2, the filtration step will be described. FIG. 2 is a cross sectional view in schematic form showing filtration using the hollow fiber membrane module 100 in FIG. 1. A fluid to be filtrated (for example, the biomedical culture medium) 20 containing a suspended substance 22 is introduced through the lower opening 1, the fluid to be filtrated 20 moves upward (in the direction of the arrow) within a channel of the hollow fiber membrane 4, the suspended substance 22 is filtered out at a pore formed in a tube wall of the hollow fiber membrane 4, a clarified permeation fluid 24 is discharged outside the hollow fiber membrane 4, and the permeation fluid 24 thus discharged can be taken out through the first nozzle 12 or the second nozzle 14. That is to say, the permeation fluid 24 that is the fluid to be filtrated 20 filtrated through the hollow fiber membrane 4 can flow inwards or outwards through the first nozzle 12 or the second nozzle 14. Meanwhile, the concentration of the suspended substance 22 in the fluid to be filtrated 20 left unfiltered increases with the fluid passing upward through the hollow fiber membrane 4, the fluid to be filtrated becomes concentrated (concentrate) in the vicinity of the upper opening 1, and the concentrate is drained through the upper opening 1.

Meanwhile, the filtration step may be performed by closing the upper opening 1 and without taking out the fluid to be filtrated that is concentrated (concentrate) through the upper opening 1.

Figure 3:
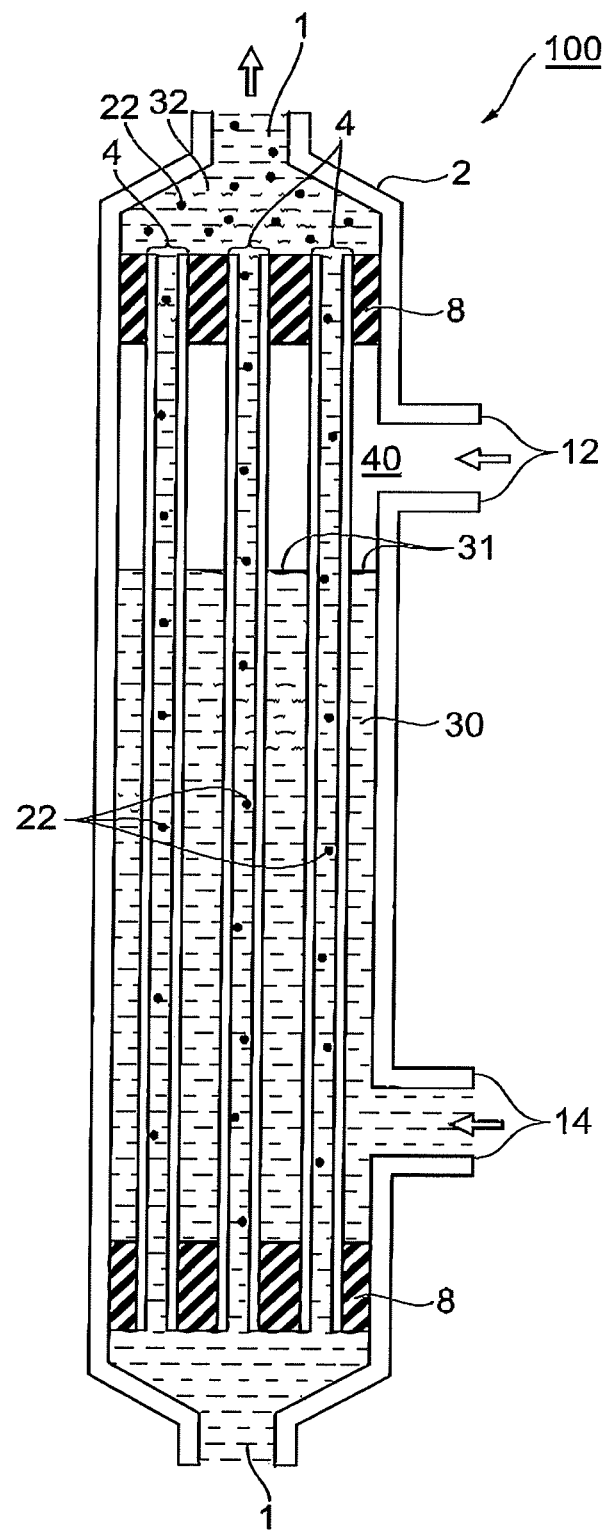
[FIG. 3] A cross sectional view in schematic form showing a clarification method using the hollow fiber membrane module of FIG. 1.

Next, with reference to FIG. 3, the backwash step will be described. FIG. 3 is a cross sectional view in schematic form showing the clarification method using the hollow fiber membrane module 100 in FIG. 1. In order to carry out the clarification method, first, the hollow fiber membrane module is disposed in such a way that either of the first nozzle 12 and the second nozzle 14 is positioned higher than the other (in FIG. 3, the first nozzle 12 is positioned higher). Then, the space (in FIG. 2, the region where the permeate 24 exists) between the hollow fiber membrane 4 and the housing 2 is filled with a backwash fluid 30 through the first nozzle 12 or the second nozzle 14.

After making the state as above, a gas 40 is introduced through the first nozzle 12 into the interior of the housing 2 to gradually lower a fluid level 31 of the backwash fluid 30, the hollow fiber membrane 4 is washed with the backwash fluid 30 to remove the suspended substance 22 existing in the tube wall of the hollow fiber membrane 4 from the tube wall, and backwash waste 32 containing the suspended substance 22 is drained through the upper opening 1.

On carrying out the above-mentioned backwash step, after filling the housing 2 with the backwash fluid 30, the second nozzle 14 and the lower opening 1 may be closed to introduce the gas 40 through the first nozzle 12 (a first method), or, while the lower opening 1 is closed, the gas 40 may be introduced through the first nozzle 12 and the backwash fluid 30 may be introduced through the second nozzle 14 (a second method). Furthermore, without closing the lower opening 1, the above-mentioned first method or second method may be carried out while introducing the fluid to be filtrated 20 containing the suspended substance 22 into the hollow fiber membrane 4.

The filtration step is preferably a cross-flow filtration step of, while introducing the fluid to be filtrated 20 through one end of the hollow fiber membrane 4 into the interior of the tube thereof for feeding the fluid along the tube wall, filtrating the fluid through the tube wall and discharging the fluid to be filtrated 24 clarified through pores, and draining the fluid to be filtrated concentrated by filtration through the other end of the hollow fiber membrane 4.

In the clarification method, the filtration step and the backwash step are alternately carried out. For example, in the backwash step, the hollow fiber membrane partly blocked in the filtration step is cleaned, and then is subjected to the filtration step again. These are repeated if necessary.

In other words, the above-mentioned clarification method is a clarification method including a step of using the hollow fiber membrane module in an upright position, introducing a suspension (the fluid to be filtrated) from a lower part of the module, and performing filtration for a predetermined period of time or under an internal pressure of a predetermined amount, and a step of, at a state where a second side of the module (the permeate side) is filled with a fluid (the backwash fluid), while introducing gas to adjust the fluid level (a gas-liquid interface), backwashing with an external pressure and draining the backwash waste from the top of the module.

The upright position herein is a state in which one end of the hollow fiber membrane module is higher than the other, including a vertical position and a slanting position to the surface of the ground. In addition, performing filtration under an internal pressure is to perform filtration by introducing a pressurized fluid from the inner surface side of the hollow fiber membrane, and backwashing with an external pressure is to introduce a pressurized fluid from the outer surface side of the hollow fiber membrane and allow it to permeate to the inner surface side of the hollow fiber membrane thereby physically removing a substance deposited on the inner surface.

The gas to be used according to this embodiment may be any gas that does not exert an influence upon the membrane or the fluid, and using air or nitrogen is preferable from the cost and safety viewpoints.

The state in which the hollow fiber membrane module is in an upright position in the step of performing inside-out filtration is not essential but the state in which the hollow fiber membrane module is in an upright position during backwash is essential, and therefore using the hollow fiber membrane module in an upright position in all of these steps is preferable to make a filtration operation easy.

The period of time to perform the inside-out filtration and the amount thereof can be suitably determined depending on properties of an intended suspension. In the step of performing backwash, the state in which the hollow fiber membrane module is in an upright position is essential to make it possible to backwash while introducing gas and controlling the fluid level.

In the case of performing backwash without controlling the fluid level, the backwash fluid flows preferentially through a part of the hollow fiber membrane where the fluid is most likely to flow, so that it is difficult to wash the hollow fiber membrane thoroughly without unevenness. On the contrary, in the case of controlling the fluid level to gradually lowering it and draining backwash waste from the top of the module (the case of the method of the present invention), during the interior of the hollow fiber membrane module is filled with the fluid, the backwash fluid most likely to flow through the upmost part of the hollow fiber membrane module and the part is preferentially backwashed. By introducing gas to this part to lower the fluid level, the backwash fluid does not flow through the part of the hollow fiber membrane that comes into contact with gas, but the hollow fiber membrane in the vicinity of the fluid level is preferentially backwashed. By performing backwash while thus lowering the fluid level, it is possible to perform backwash sequentially while changing the part that is being washed from the top to the bottom of the hollow fiber membrane within the hollow fiber membrane module. Thus, it is possible to backwash with high efficiency, and therefore it is possible to reduce the treatment time, improve recovery, or the like, namely increase efficiency of clarification or turbidity removal.

As described above, to perform filtration while draining the concentrate of the suspended substance (the fluid that remains without permeating while filtration is performed from the inner surface side of the hollow fiber membrane, and in which a higher concentration of suspended matter than in an original fluid is contained) from the top of the hollow fiber membrane module is preferable. By thus performing filtration while draining the concentrate, and thereby decreasing the amount of the suspended substance that is pressed to the interior and the surface of the membrane, clogging of the membrane decreases and it is possible to improve washing performance in backwash.

The clarification method using the hollow fiber membrane module according to this embodiment is suitable for use in clarification in which a suspended matter component in a suspension is a substance of biological origin. The suspended matter component of biological origin may be of animal origin or of plant origin, and examples thereof include, for example, cell culture mediums, yeast fermentation liquids, etc. In the case of clarifying the suspended matter component of biological origin as above by membrane filtration, in a filtration method to be generally used, the filtration pressure increases with the duration of filtration, deformation, destruction, etc. of suspended substances takes place, the resultant permeates through a membrane to contaminate the permeation fluids or adhere to the membrane. In the clarification method using the hollow fiber membrane module according to this embodiment, a backwash effect is high and it is possible to keep the filtration pressure low for a prolonged period of time, so that deformation and destruction of suspended substances does not take place, a permeation fluid of high quality can be obtained, and it is possible to improve filtration efficiency.

EXAMPLE

Hereinafter, based on Examples and Comparative Examples, the present invention will be more specifically described, however, the present invention is not limited to the following Examples.

As for the porous hollow fiber membrane in the following Examples and Comparative Examples, a measurement of the average pore size in the inner face and the position of the minimum pore size-layer, a measurement of the pore size in the minimum pore size-layer, a measurement of the inner diameter, the outer diameter, and the membrane thickness, a measurement of the polyvinylpyrrolidone content, a measurement of the polyvinylpyrrolidone distribution, a measurement of the solution viscosity of a raw fluid for membrane production, and a measurement of the weight average molecular weight of polyvinylpyrrolidone were performed with the following method.

(1) A Measurement of the Pore Size in the Inner Face and the Position of the Minimum Pore Size-layer The inner face of a lyophilized porous hollow fiber membrane was observed with an electron microscope at a magnification in which not less than 10 pores can be observed per 1 field of view. Circle approximation was applied to the pores in the obtained microscope photograph, and the diameter determined from the area average value was referred to as the average pore size in the inner face (the pore size in the inner face). A cross section of the lyophilized porous membrane was successively observed from the inner face side toward the outer face side to identify the position of a layer at which the cross section pore size is minimum.

(2) A Method for Determining the Pore Size in the Minimum Pore Size-layer

Polystyrene latex particles were dispersed into 0.5 wt % of an aqueous solution of sodium dodecyl sulfate at a particle concentration of 0.01 wt % to adjust latex particle dispersion. Filtration of the latex particle dispersion was performed using a porous hollow fiber membrane to measure a change in concentration of the latex particle before and after filtration. This measurement was performed while changing the latex particle size by about 0.1 µm starting from 0.1 µm to generate a rejection curve of the latex particle. The particle size with which permeation can be rejected by 90% was read out using this rejection curve, and was referred to as the pore size in the minimum pore size-layer (the rejection pore size).

In the case where the minimum pore size-layer was identified to be in an outer circumferential region by the above-mentioned "(1) a measurement of the position of the minimum pore size-layer", the pore size in the minimum pore size-layer (the rejection pore size) that is determined by the above-mentioned "(2) a method for determining the pore size in the minimum pore size-layer" is the rejection pore size in the outer circumferential region.

(3) A Measurement of the Inner Diameter, the Outer Diameter and the Membrane Thickness of a Porous Hollow Fiber Membrane A porous hollow fiber membrane was cylindrically sliced and was observed with a measuring microscope to measure the inner diameter (µm) and the outer diameter (µm) of the porous hollow fiber membrane. The membrane thickness was calculated from the inner diameter and the outer diameter thus obtained, using the following formula (II).

$$\text{Membrane thickness}(\mu m) = (\text{outer diameter} - \text{inner diameter})/2 \quad \text{(II)}$$

(4) A Measurement of the Polyvinylpyrrolidone Content (in the Case of Polysulfone Membrane)

A $^1$H-NMR measurement of a porous hollow fiber membrane was carried out under the following conditions and, in the spectra thus obtained, a calculation was performed from the integral ($I_{PVP}$) of a signal attributable to polyvinylpyrrolidone (4H) that appears in the vicinity of 1.85 to 2.5 ppm, and the integral ($I_{PSf}$) of a signal attributable to polysulfone (4H) that appears in the vicinity of 7.3 ppm, using the following formula (III).

[Measurement Conditions]
Equipment: JNM-LA400 (JEOL Ltd.)
Resonance frequency: 400.05 MHz
Solvent: deuterated DMF
Sample concentration: 5% by weight
Number of transients: 256

$$\text{Polyvinylpyrrolidone content (\% by mass)} = 111(I_{PVP}/4)/\{442(I_{PSf}/4) + 111(I_{PVP}/4)\} \times 100 \quad \text{[Formula (III)]}$$

The "polyvinylpyrrolidone content" thus calculated is the polyvinylpyrrolidone content relative to the total mass of the porous hollow fiber membrane. Meanwhile, in the case where a hydrophobic polymer is a polymer other than polysulfone, the polyvinylpyrrolidone content can be determined, as in the case of polysulfone, from the integral of signals each attributable to the hydrophobic polymer or polyvinylpyrrolidone and the molecular weight of a monomer unit constituting the hydrophobic polymer.

(5) A Measurement of the Polyvinylpyrrolidone Distribution

When divided a tube wall of a porous hollow fiber membrane in the membrane-thickness direction equally into three regions, a sample of a part of an outer circumferential region including the outer face and a sample of a part of an inner circumferential region including the inner face were collected, and contents of polyvinylpyrrolidone contained in the porous hollow fiber membrane were determined by an NMR measurement as in the above-mentioned measurement. The polyvinylpyrrolidone distribution was determined from the polyvinylpyrrolidone content in the outer circumferential region ($C_{out}$) and the content thereof in the inner circumferential region ($C_{in}$) thus obtained using the following formula (IV).

$$\text{Polyvinylpyrrolidone distribution} = C_{out}/C_{in} \quad \text{(IV)}$$

(6) A Measurement of the Solution Viscosity of a Raw Fluid for Membrane Production A raw fluid for membrane production contained in a wide-mouthed bottle was placed in a thermostat, and the temperature of the fluid was set to be the temperature thereof to be extruded through a double tubular nozzle. A measurement of viscosity was performed with a B type viscometer.

(7) A Measurement of the Weight Average Molecular Weight of Polyvinylpyrrolidone A sample fluid was prepared by dissolving polyvinylpyrrolidone in DMF at a concentration of 1.0 mg/ml, and a GPC measurement was performed under the following conditions to determine the weight average molecular weight (on PMMA basis) thereof.
Equipment: HLC-8220GPC (Tosoh Corporation)
Column: Shodex KF-606M, KF-601
Oven: 40° C.
Mobile phase: 0.6 ml/min DMF
Detector: a differential refractive index detector A calibration curve (a cubic equation) using PMMAs that are reference materials for GPC having the following weight average molecular weights was prepared, and the weight average molecular weight on PMMA basis was determined based on the calibration curve and the efflux time of polyvinylpyrrolidone.
1944000, 790000, 281700, 144000, 79250, 28900, 13300, 5720, 1960

Example 1

[Production of a Porous Hollow Fiber Membrane]

18% by weight of polysulfone (product of SOLVAY ADVANCED POLYMERS, Udel P3500) and 15% by weight of polyvinylpyrrolidone (product of BASF, Luvitec K80, a weight average molecular weight of $4.4 \times 10^5$) were dissolved in 62% by weight of N-methyl-2-pyrrolidone at 70° C. while stirring, 5% by weight of glycerol was added thereto, and the mixture was further stirred to adjust a raw fluid for membrane production. The raw fluid for membrane production was extruded through a double annular spinning nozzle (an outermost diameter of 2.4 mm, an intermediate diameter of 1.2 mm, and an innermost diameter of 0.6 mm, and one used the same nozzle in the following Examples as well) together with a 90% by weight NMP aqueous solution as an inner congealing fluid to pass through an airflow distance of 50 mm to be coagulated in water at 80° C. After desolvation in water and after a treatment for PVP removal in a 2000 ppm aqueous solution of sodium hypochlorite, washing with water was performed to obtain a porous hollow fiber membrane. Evaluation results for the obtained porous hollow fiber membrane are shown in Table 1. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]

The obtained porous hollow fiber membrane was placed in a module casing with an effective length of 20 cm in such a way that a membrane area is 50 cm$^2$ to prepare a mini module. A biomedical culture medium was fed to the module at a linear speed of 0.5 m/sec, and the permeate flow rate was measured within a certain period of time. Meanwhile, during the course of measuring, countercurrent washing was performed once every 5 minutes. The countercurrent washing was performed by stopping a circulation pump, forcing about 12 to 15 ml of air into the mini module from the permeate side thereof with a syringe, and making the permeate remaining at the permeate side of the module pass through toward the interior of the hollow fiber. As the biomedical culture medium, a culture medium (a cell density of about $1.7 \times 10^7$/ml, cell viability of about 56%) in which Chinese hamster ovary (CHO) cells are cultured in a serum-free medium (Irvine Scientific IS CHO-CD medium) was used. Measurement results are shown in Table 1.

As compared with the results in Comparative Example 3 and Reference Example 1 to be described below, it was obvious that it is possible to perform a purification step (clarification) of the cell culture medium by membrane filtration alone as a single step. In addition, there was no contamination of cells and disrupted cell products, etc. in the permeate. Furthermore, the cumulative filtration capacity in 60 minutes was not lower than 1000 g, and therefore it was obvious that production efficiency was excellent.

Example 2

[Production of a Porous Hollow Fiber Membrane]

A porous hollow fiber membrane was prepared as in Example 1. Evaluation results for the obtained porous hollow fiber membrane are shown in Table 1. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]

A clarification test of a biomedical culture medium was performed as in Example 1 except that a mini module was prepared using the obtained porous hollow fiber membrane and a biomedical culture medium was fed at a linear speed of 1 m/sec. Measurement results are shown in Table 1.

As compared with the results in Comparative Example 3 and Reference Example 1 to be described below, it was obvious that it is possible to perform a purification step (clarification) of a cell culture medium by membrane filtration alone as a single step. In addition, there was no contamination of cells and disrupted cell products, etc. in permeate. Furthermore, the cumulative filtration capacity in 60 minutes was not lower than 1000 g, and therefore it was obvious that production efficiency was excellent.

Example 3

[Production of a Porous Hollow Fiber Membrane]

A porous hollow fiber membrane was prepared as in Example 1. Evaluation results for the obtained porous hollow fiber membrane are shown in Table 1. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]

A clarification test of a biomedical culture medium was performed as in Example 1 except that a mini module was prepared using the obtained porous hollow fiber membrane and countercurrent washing was not performed. Measurement results are shown in Table 1.

As compared with the results in Comparative Example 3 and Reference Example 1 to be described below, it was obvious that it is possible to perform a purification step (clarification) of a cell culture medium by membrane filtration alone as a single step. In addition, there was no contamination of cells and disrupted cell products, etc. in permeate. Furthermore, the cumulative filtration capacity in 60 minutes was not lower than 1000 g, and therefore it was obvious that production efficiency was excellent.

Example 4

[Production of a Porous Hollow Fiber Membrane]

A porous hollow fiber membrane was performed as in Example 1 except that polyvinylpyrrolidone (product of BASF, Luvitec K85, a weight average molecular weight of $6.4 \times 10^5$) was used in lieu of polyvinylpyrrolidone (product of BASF, Luvitec K80). Evaluation results for the obtained porous hollow fiber membrane are shown in Table 1. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]

A clarification test of a biomedical culture medium was performed as in Example 1. Measurement results are shown in Table 1.

As compared with the results in Comparative Example 3 and Reference Example 1 to be described below, it was obvious that it is possible to perform a purification step (clarification) of a cell culture medium by membrane filtration alone as a single step. In addition, there was no contamination of cells and disrupted cell products, etc. in permeate. Furthermore, the cumulative filtration capacity in 60 minutes was not lower than 1000 g, and therefore it was obvious that production efficiency was excellent.

Example 5

[Production of a Porous Hollow Fiber Membrane]

A porous hollow fiber membrane was prepared as in Example 1 except that polyvinylpyrrolidone (product of BASF, Luvitec K90, a weight average molecular weight of $7.8 \times 10^5$) was used in lieu of polyvinylpyrrolidone (product of BASF, Luvitec K80). Evaluation results for the obtained porous hollow fiber membrane are shown in Table 1. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]

A clarification test of a biomedical culture medium was performed as in Example 1. Measurement results are shown in Table 1.

As compared with the results in Comparative Example 3 and Reference Example 1 to be described below, it was obvious that it is possible to perform a purification step (clarification) of a cell culture medium by membrane filtration alone as a single step. In addition, there was no contamination of cells and disrupted cell products, etc. in permeate. Furthermore, the cumulative filtration capacity in 60 minutes was not lower than 1000 g, and therefore it was obvious that production efficiency was excellent.

Example 6

[Production of a Porous Hollow Fiber Membrane]
A porous hollow fiber membrane was prepared as in Example 1 except that polyvinylpyrrolidone (product of BASF, Luvitec K60, a weight average molecular weight of $2.9 \times 10^5$) was used in lieu of polyvinylpyrrolidone (product of BASF, Luvitec K80). Evaluation results for the obtained porous hollow fiber membrane are shown in Table 1. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]
A clarification test of a biomedical culture medium was performed as in Example 1. Measurement results are shown in Table 1. There was no contamination of cells and disrupted cell products, etc. in permeate and the cumulative filtration capacity in 60 minutes was not lower than 700 g, indicating sufficient filtration performance.

Example 7

[Production of a Porous Hollow Fiber Membrane]
A porous hollow fiber membrane was prepared as in Example 1 except that polyvinylpyrrolidone (product of BASF, Luvitec K115, a weight average molecular weight of $9.9 \times 10^5$) was used in lieu of polyvinylpyrrolidone (product of BASF, Luvitec K80). Evaluation results for the obtained porous hollow fiber membrane are shown in Table 1. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]
A clarification test of a biomedical culture medium was performed as in Example 1. Measurement results are shown in Table 1. There was no contamination of cells and disrupted cell products, etc. in permeate and the cumulative filtration capacity in 60 minutes was not lower than 700 g, indicating sufficient filtration performance.

Example 8

[Production of a Porous Hollow Fiber Membrane]
18% by weight of polysulfone (product of SOLVAY ADVANCED POLYMERS, Udel P3500) and 5% by weight of polyvinylpyrrolidone (product of BASF, Luvitec K80) were dissolved in 72% by weight of N-methyl-2-pyrrolidone at 70° C. while stirring, 5% by weight of glycerol was added thereto, and the mixture was further stirred to adjust a raw fluid for membrane production. A porous hollow fiber membrane was prepared as in Example 1 except that. Evaluation results for the obtained porous hollow fiber membrane are shown in Table 2. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]
A clarification test of a biomedical culture medium was performed as in Example 1. Measurement results are shown in Table 2.

As compared with the results in Comparative Example 3 and Reference Example 1 to be described below, it was obvious that it is possible to perform a purification step (clarification) of a cell culture medium by membrane filtration alone as a single step. In addition, there was no contamination of cells and disrupted cell products, etc. in permeate. Furthermore, the cumulative filtration capacity in 60 minutes was not lower than 1000 g, and therefore it was obvious that production efficiency was excellent.

Example 9

[Production of a Porous Hollow Fiber Membrane]
18% by weight of polysulfone (product of SOLVAY ADVANCED POLYMERS, Udel P3500) and 20% by weight of polyvinylpyrrolidone (product of BASF, Luvitec K80) were dissolved in 57% by weight of N-methyl-2-pyrrolidone at 70° C. while stirring, 5% by weight of glycerol was added thereto, and the mixture was further stirred to adjust a raw fluid for membrane production. A porous hollow fiber membrane was prepared as in Example 1 except that. Evaluation results for the obtained porous hollow fiber membrane are shown in Table 2. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]
A clarification test of a biomedical culture medium was performed as in Example 1. Measurement results are shown in Table 2.

As compared with the results in Comparative Example 3 and Reference Example 1 to be described below, it was obvious that it is possible to perform a purification step (clarification) of a cell culture medium by membrane filtration alone as a single step. In addition, there was no contamination of cells and disrupted cell products, etc. in permeate. Furthermore, the cumulative filtration capacity in 60 minutes was not lower than 1000 g, and therefore it was obvious that production efficiency was excellent.

Comparative Example 1

[Production of a Porous Hollow Fiber Membrane]
18% by weight of polysulfone (product of SOLVAY ADVANCED POLYMERS, Udel P3500) and 2% by weight of polyvinylpyrrolidone (product of BASF, Luvitec K80) were dissolved in 75% by weight of N-methyl-2-pyrrolidone at 70° C. while stirring, 5% by weight of glycerol was added thereto, and the mixture was further stirred to adjust a raw fluid for membrane production. A porous hollow fiber membrane was prepared as in Example 1 except that. Evaluation results for the obtained porous hollow fiber membrane are shown in Table 2. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]

A clarification test of a biomedical culture medium was performed as in Example 1. Measurement results are shown in Table 2. While there was no contamination of cells and disrupted cell products, etc. in permeate and the cumulative filtration capacity in 60 minutes was higher than 700 g in total, the membrane tended to be clogged before a lapse of 60 minutes, and a decrease in the over time filtration rate was seen. It is considered that a tendency to generate clogging is high because of a low PVP amount.

Comparative Example 2

[Production of a Porous Hollow Fiber Membrane]

18% by weight of polysulfone (product of SOLVAY ADVANCED POLYMERS, Udel P3500) and 24% by weight of polyvinylpyrrolidone (product of BASF, Luvitec K80) were dissolved in 53% by weight of N-methyl-2-pyrrolidone at 70° C. while stirring, 5% by weight of glycerol was added thereto, and the mixture was further stirred to adjust a raw fluid for membrane production. A porous hollow fiber membrane was prepared as in Example 1 except that. Evaluation results for the obtained porous hollow fiber membrane are shown in Table 2. The porous hollow fiber membrane had a gradient structure in which the pore size successively decreases from the inner face toward the minimum pore size-layer, and the minimum pore size-layer positioned in an outer circumferential region of the porous hollow fiber membrane.

[A Clarification Test of a Biomedical Culture Medium]

A clarification test of a biomedical culture medium was performed as in Example 1 except that the linear speed was changed to 1.5 m/sec. Measurement results are shown in Table 2. While there was no contamination of cells and disrupted cell products, etc. in permeate and the cumulative filtration capacity in 60 minutes was higher than 700 g in total, a contamination of impurities such as disrupted cell products in permeate increased. When the polyvinylpyrrolidone content is high and thereby polyvinylpyrrolidone swells, there is no other option but to increase the linear speed so as to increase the pressure to be applied on the membrane, for securing the cumulative filtration capacity. It is considered that, because the linear speed increased, history and influence on cells increased thereby facilitating disruption.

Comparative Example 3

[Production of a Porous Hollow Fiber Membrane]

15.0% by volume of hydrophobic silica the powder of which completely gets wet with 50% by volume (MW value) of methanol, the average primary particle size of which is 16 μm, and the specific surface area of which is 110 m²/g, 42.0% by volume of dibutyl phthalate, and 18.2% by volume of dioctyl phthalate were mixed with a Henschel mixer, 24.8% by volume of a polyethylene resin (Suntec SH-800) with Mw=270000 and Mn=43000 was added thereto, and the mixture was mixed again with the Henschel mixer.

The obtained mixture was extruded with a twin screw extruder of 87 mm φ to make that into a pellet. The pellet was formed into a hollow fiber with a device for hollow fiber production in which a hollow spinning opening is equipped to a twin screw extruder of 30 mm φ. The hollow fiber membrane thus formed was immersed in 1,1,1-trichloroethane at 60° C. for 1 hour to extract dibutyl phthalate and dioctyl phthalate, and then, the membrane was dried.

After drying, the hollow fiber membrane was immersed in a 50% ethyl alcohol aqueous solution for 30 minutes, and was transferred in water and immersed for another 30 minutes for hydrophilization. Furthermore, after the hollow fiber membrane was immersed in a 20% caustic soda aqueous solution at 70° C. for 1 hour to extract hydrophobic silica, the membrane was washed and dried to obtain a polyethylene porous hollow fiber membrane.

The outer diameter of the obtained porous hollow fiber membrane was 2300 μm, the inner diameter was 1400 μm, the average pore size was 0.39 μm, the water permeation amount at 25° C. was 1200 L/(m²·hr·atm), breaking strength was 65 kgf/cm², and breaking elongation was 600%. Pore sizes from the membrane outer surface to the membrane inner surface were uniform.

The porous hollow fiber membrane was immersed in an aqueous solution (concentration of 0.5% by weight) of polyvinylpyrrolidone (product of BASF, Luvitec K80) to coat throughout the membrane thickness with polyvinylpyrrolidone (PVP). Furthermore, the porous hollow fiber membrane is irradiated with a gamma ray of 25 KGy to insolubilize PVP.

As for hydrophobic silica, the volume % (MW value) of methanol to make the powder completely wet is determined in the following procedures.

1) 0.2 g of hydrophobic silica is placed in a beaker as a sample, and 50 ml of deionized water is added thereto.
2) While stirring electromagnetically, methanol is gradually added into the part lower than the fluid level, the point at which hydrophobic silica is not seen at the fluid level is referred to as an end point, and the amount X (ml) of methanol required by the end point is substituted in the following formula to calculate the MW value.

$$MW \text{ value} = \frac{X}{50 + X} \times 100 \qquad \text{[Numerical formula 1]}$$

X: the amount of methanol used (ml)

Namely, the MW value is the ratio of "the amount (ml) of methanol required" to "the sum of the amount 50 ml of deionized water and the amount (ml) of methanol required".

[A Clarification Test of a Biomedical Culture Medium]

A clarification test of a biomedical culture medium was performed as in Example 1. Measurement results are shown in Table 2. While there was no contamination of cells and disrupted cell products, etc. in permeate, rapid clogging took place, and thereby the cumulative filtration capacity in 60 minutes was lower than one-tenth of that in Example 1.

Reference Example 1

[A Clarification Test of a Biomedical Culture Medium]

A biomedical culture medium was subjected to a clarification treatment using a centrifuge (Culturefuge 100 manufactured by Alfa Laval) at a rotational speed of 7500 rpm and a flow rate of 600 L/hr. On the porous hollow membrane prepared in Comparative Example 3, a clarification test of a biomedical culture medium that was subjected to a clarification treatment was performed as in Example 1. The obtained results are shown in Table 2. Since the biomedical culture medium was filtered after the clarification treatment by centrifugation, a cumulative filtration capacity in 60 minutes significantly improved compared to Comparative Example 3.

Example 10

[A Clarification Test of a Biomedical Culture Medium]

A clarification test was performed as in Example 1 except that a biomedical culture medium was fed to a mini module at a linear speed of 0.1 m/sec. The obtained results are shown in Table 3. There was no contamination of cells and disrupted cell products, etc. in permeate. The cumulative filtration capacity in 60 minutes was higher than that in Comparative Example.

Example 11

[A Clarification Test of a Biomedical Culture Medium]

A clarification test was performed as in Example 1 except that a biomedical culture medium was fed to a mini module at a linear speed of 1.2 m/sec. The obtained results are shown in Table 3. The cumulative filtration capacity in 60 minutes was not lower than 1000 g, and therefore it was obvious that production efficiency was excellent. However, a contamination of disrupted cell products, etc. in permeate was identified to some extent.

TABLE 1

| | Example 1 | Example 2 | Example 3 | Example 4 | Example 5 | Example 6 | Example 7 |
|---|---|---|---|---|---|---|---|
| Gradient structure | Present | Present | Present | Present | Present | Present | Present |
| Average pore size in inner face (μm) | 30 | 30 | 30 | 30 | 30 | 30 | 30 |
| Pore size in minimum pore size-layer (rejection pore size, μm) | 0.4 | 0.4 | 0.4 | 0.4 | 0.4 | 0.4 | 0.4 |
| Polyvinylpyrrolidone content (wt %) | 1.2 | 1.2 | 1.2 | 1.2 | 1.2 | 1.2 | 1.2 |
| Inner diameter (μm) | 1410 | 1380 | 1420 | 1410 | 1410 | 1410 | 1410 |
| Outer diameter (μm) | 2320 | 2280 | 2300 | 2320 | 2320 | 2320 | 2320 |
| Membrane thickness (μm) | 455 | 450 | 440 | 455 | 455 | 455 | 455 |
| Polyvinylpyrrolidone concentration distribution (Cout/Cin) | 2.67 | 2.70 | 2.66 | 2.67 | 2.67 | 2.67 | 2.67 |
| Weight average molecular weight of polyvinylpyrrolidone | $4.4 \times 10^5$ | $4.4 \times 10^5$ | $4.4 \times 10^5$ | $6.4 \times 10^5$ | $7.8 \times 10^5$ | $2.9 \times 10^5$ | $9.9 \times 10^5$ |
| Linear speed (m/sec) | 0.5 | 1.0 | 0.5 | 0.5 | 0.5 | 0.5 | 0.5 |
| Countercurrent washing | Present | Present | None | Present | Present | Present | Present |
| Cumulative filtration capacity in 30 minutes (g) | 546 | 480 | 556 | — | — | — | — |
| Cumulative filtration capacity in 60 minutes (g) | 1720 | 1540 | 1140 | 1630 | 1900 | 770 | 810 |

TABLE 2

| | Example 8 | Example 9 | Comparative Example 1 | Comparative Example 2 | Comparative Example 3 | Reference Example 1 |
|---|---|---|---|---|---|---|
| Gradient structure | Present | Present | Present | Present | None | None |
| Average pore size in Inner face (μm) | 30 | 30 | 30 | 30 | 0.39 | 0.39 |
| Pore size in minimum pore size-layer (rejection pore size, μm) | 0.4 | 0.4 | 0.4 | 0.4 | 0.39 | 0.39 |
| Polyvinylpyrrolidone content (wt %) | 0.3 | 2.8 | 0.1 | 3.3 | 1.2 | 1.2 |
| Inner diameter (μm) | 1410 | 1410 | 1410 | 1410 | 1400 | 1400 |
| Outer diameter (μm) | 2320 | 2320 | 2320 | 2320 | 2300 | 2300 |
| Membrane thickness (μm) | 455 | 455 | 455 | 455 | 455 | 455 |
| Polyvinylpyrrolidone concentration distribution (Cout/Cin) | 2.10 | 2.88 | 1.79 | 3.21 | 1.00 | 1.00 |
| Weight average molecular weight of polyvinylpyrrolidone | $4.4 \times 10^5$ | $4.4 \times 10^5$ | $4.4 \times 10^5$ | $4.4 \times 10^5$ | $4.4 \times 10^5$ | $4.4 \times 10^5$ |
| Linear speed (m/sec) | 0.5 | 0.5 | 0.5 | 1.5 | 0.5 | 0.5 |
| Countercurrent washing | Present | Present | Present | Present | Present | Present |
| Cumulative filtration capacity in 60 minutes (g) | 1070 | 1020 | 890 | 910 | 103 | 307 |

TABLE 3

|  | Example 10 | Example 11 |
|---|---|---|
| Gradient structure | Present | Present |
| Average pore size in inner face (μm) | 30 | 30 |
| Pore size in minimum pore size-layer (rejection pore size, μm) | 0.4 | 0.4 |
| Polyvinylpyrrolidone content (wt %) | 1.2 | 1.2 |
| Inner diameter (μm) | 1410 | 1410 |
| Outer diameter (μm) | 2320 | 2320 |
| Membrane thickness (μm) | 455 | 455 |
| Polyvinylpyrrolidone concentration distribution (Cout/Cin) | 2.67 | 2.67 |
| Weight average molecular weight of polyvinylpyrrolidone | $4.4 \times 10^5$ | $4.4 \times 10^5$ |
| Linear speed (m/sec) | 0.1 | 1.2 |
| Countercurrent washing | Present | Present |
| Cumulative filtration capacity in 60 minutes (g) | 981 | 1440 |

A clarification test of a simulation suspension and an identification of the position of the minimum pore size-layer were performed in the following methods.

(1) A Clarification Test of a Simulation Suspension

A polysulfone hollow fiber membrane that has a minimum pore size-layer of 0.4 μm in the vicinity of the outer surface (the outer face) and that is with a gradient structure in which the pore size successively decreases from the inner surface (the inner face) toward the minimum pore size-layer was placed into a module casing with an effective length of 20 cm in such a way that the membrane area is 50 cm² to prepare a mini module. Using the module vertically disposed in an upright position, a clarification test of a simulation suspension was performed. As the simulation suspension, a CHO cell culture medium with a cell density of about $1 \times 10^7$ cells/ml was used.

In addition, the recovery rate R (%) for a permeation fluid was determined by the following formula.

$$R = (Vf - Vc - Vr)/Vf$$

Here, Vf: the amount of fed fluid (ml)
Vc: the amount of concentrate (ml)
Vr: the amount of backwash fluid (ml)

(2) Identification of the Position of the Minimum Pore Size-layer

A cross section of the porous membrane that was lyophilized was successively observed from the inner surface side toward the outer surface side with an electron microscope to identify the position of a layer at which the cross section pore size is minimum.

Reference Example 2

Dead-end Filtration

A simulation suspension was fed at 230 ml/min, and filtration was performed without draining concentrate from the top of a module. Backwash was carried out at an interval of 5 minutes while the fluid level was controlled by introducing air with a syringe at a pressure of not higher than about 50 kPa. Results of a clarification test were summarized in Table 4 that covers the following Examples.

Reference Example 3

Cross-flow

A clarification test was performed as in Reference Example 2 except that filtration was performed while 5% concentrate of a simulation suspension that was fed from the top of a module was drained.

Reference Example 4

A Homogeneous Membrane

A clarification test was performed as in Reference Example 3 except that a polyvinylidene fluoride homogeneous membrane with a pore size of 0.2 μm was used as a hollow fiber membrane.

Reference Example 5

Standard Backwash

A clarification test was performed as in Reference Example 3 except that backwash was performed without introducing gas during backwash.

Reference Example 6

A Homogeneous Membrane and Standard Backwash

A clarification test was performed as in Reference Example 4 except that backwash was performed without introducing gas during backwash.

TABLE 4

|  | Reference Example 2 | Reference Example 3 | Reference Example 4 | Reference Example 5 | Reference Example 6 |
|---|---|---|---|---|---|
| Position of minimum pore size-layer | Outer surface | Outer surface | Throughout membrane thickness | Outer surface | Throughout membrane thickness |
| Pore size in minimum pore size-layer μm | 0.4 | 0.4 | 0.2 | 0.4 | 0.2 |
| Fluid level adjustment by introducing gas during backwash | Present | Present | Present | None | None |
| Concentrate draining | None | Present | Present | Present | Present |
| Pressure difference within membrane after 30 minutes of turbidity removal treatment (kPa) | 37.5 | 5.5 | 46.5 | 11.5 | 58 |

TABLE 4-continued

|  | Reference Example 2 | Reference Example 3 | Reference Example 4 | Reference Example 5 | Reference Example 6 |
|---|---|---|---|---|---|
| Amount of gas introduced during backwash (ml) | 9 | 9 | 9 | 0 | 0 |
| Amount of fluid used during backwash (ml) | 9 | 9 | 9 | 30 | 30 |
| Recovery rate of permeation fluid (%) | 99.2 | 94.2 | 94.2 | 92.4 | 92.4 |

Reference Signs List

1 ... Opening, 2 ... Housing, 4 ... Hollow fiber membrane, 6 ... Hollow fiber membrane bundle, 8 ... immobilizing member, 12 ... First nozzle, 14 ... Second nozzle, 20 ... Fluid to be filtrated, 22 ... Suspended substance, 24 ... Permeation fluid, 30 ... Backwash fluid, 31 ... Fluid level, 32 ... Backwash waste, 40 ... Gas, 100 ... Hollow fiber membrane module

The invention claimed is:

1. A method of use of a porous hollow fiber membrane for producing a clarified biomedical culture medium by a method including a filtration step of distributing a biomedical culture medium over the porous hollow fiber membrane, a tube wall of the hollow fiber membrane being constituted of a blend of a hydrophobic polymer and polyvinylpyrrolidone, wherein a content of the polyvinylpyrrolidone is not lower than 0.2% by mass and not higher than 3% by mass relative to a total mass of the porous hollow fiber membrane, and, when the tube wall is divided in a membrane-thickness direction equally into three regions, a content of the polyvinylpyrrolidone in an outer circumferential region including an outer face is higher than a content of the polyvinylpyrrolidone in an inner circumferential region including an inner face, and an average pore size in the inner face is larger than an average pore size in the outer face, wherein the porous hollow fiber membrane has an inner diameter of not smaller than 1000 μm and not larger than 2000 μm, and wherein the porous hollow fiber membrane satisfies the following formula (I):

$$C_{out}/C_{in} \geq 2 \quad (I)$$

wherein $C_{out}$ represents the content of the polyvinylpyrrolidone in the outer circumferential region, and $C_{in}$ represents the content of the polyvinylpyrrolidone in the inner circumferential region.

2. The method according to claim 1, wherein a weight average molecular weight of the polyvinylpyrrolidone is not lower than 400000 and not higher than 800000.

3. The method according to claim 1, wherein the porous hollow fiber membrane has an average pore size in the inner face is not smaller than 1 μm and not larger than 50 μm, the outer circumferential region has a rejection pore size of not smaller than 0.1 μm but smaller than 1 μm, and a membrane thickness of the tube wall is not smaller than 300 μm and not larger than 1000 μm.

4. The method according to claim 1, wherein the hydrophobic polymer is polysulfone.

5. The method according to claim 1, wherein the filtration is performed by cross-flow filtration including, while feeding the biomedical culture medium through one fiber end of the porous hollow fiber membrane, discharging the biomedical culture medium filtrated and clarified, and draining the biomedical culture medium left unfiltered in which a suspended substance is concentrated through the other fiber end of the porous hollow fiber membrane, and a feeding speed of the biomedical culture medium is not lower than 0.2 m/sec and not higher than 1.0 m/sec as a linear speed.

6. The method according to claim 1, wherein the method including the filtration step of distributing the biomedical culture medium over the porous hollow fiber membrane further includes a step of countercurrently washing the porous hollow fiber membrane by using permeate obtained in the filtration step.

7. The method according to claim 1, wherein the porous hollow fiber membrane is a porous hollow fiber membrane treated by steam sterilization.

8. The method according to claim 1, wherein the method including the filtration step of distributing the biomedical culture medium over the porous hollow fiber membrane is a method of clarifying the biomedical culture medium by using a hollow fiber membrane module comprising:

a housing having openings at both ends;

a hollow fiber membrane bundle having a plurality of the porous hollow fiber membrane, the bundle being carried inside the housing, one end of the bundle being immobilized at a side of one of the openings and the other end of the bundle being immobilized at a side of the other of the openings, so as to make it possible for the biomedical culture medium that is a fluid to be filtrated to flow inwards or outwards through the openings of the housing;

a first nozzle provided on a side face of the housing in the vicinity of one end thereof and allowing a permeation fluid to flow inwards or outwards therethrough, the permeation fluid being the fluid to be filtrated and filtrated through the porous hollow fiber membrane; and a second nozzle provided on a side face of the housing in the vicinity of the other end thereof and allowing the permeation fluid to flow inwards or outwards therethrough, and, wherein while disposing the hollow fiber membrane module in such a way that one of the first nozzle and the second nozzle is higher than the other, a filtration step of performing filtration by distributing the fluid to be filtrated over an interior of a tube of the hollow fiber membrane; and a backwash step of filling a space between the porous hollow fiber membrane and the housing with a backwash fluid and introducing gas into an interior of the housing through the nozzle at a higher position to gradually lower a fluid level of the backwash fluid, washing the porous hollow fiber membrane with the backwash fluid, and draining backwash waste through the opening at an upper side, are carried out alternately.

9. The method according to claim 8, wherein the filtration step is a cross-flow filtration step of, while feeding the fluid to be filtrated through one fiber end of the porous hollow fiber membrane, discharging the fluid to be filtrated that is filtrated and clarified, and draining the fluid to be filtrated left unfiltered in which a suspended substance is concentrated through the other fiber end of the porous hollow fiber membrane.

10. The method according to claim 1, wherein the porous hollow fiber membrane contains a minimum pore size-layer in the outer circumferential region, and has a gradient structure in which the pore size successively decreases from the inner face toward the minimum pore-size layer.

11. The method according to claim 1, wherein the porous hollow fiber membrane is obtained by a method including a coagulation step of performing discharging of a raw fluid and simultaneously discharging an inner congealing fluid to the inside of the raw fluid for coagulation in the outer congealing fluid.

12. The method according to claim 11, wherein the inner congealing fluid is an aqueous solution containing N-methylpyrrolidone at not lower than 80% by weight but lower than 100% by weight relative to the total mass of the inner congealing fluid.

13. The method according to claim 1, wherein the hydrophobic polymer is at least one of polysulfone and polyvinylidene fluoride.

* * * * *